(12) United States Patent
Lukac et al.

(10) Patent No.: US 7,867,224 B2
(45) Date of Patent: Jan. 11, 2011

(54) LASER SYSTEM FOR MEDICAL REMOVAL OF BODY TISSUE

(75) Inventors: Matjaz Lukac, Ljubljana (SL); Marko Marincek, Ljubljana (SL); Marko Kazic, Dob (SL); Karolj Nemes, Ljubljana (SL)

(73) Assignee: Fotona d.d., Ljubljana (SI)

( * ) Notice: Subject to any disclaimer, the term of this patent is extended or adjusted under 35 U.S.C. 154(b) by 0 days.

(21) Appl. No.: 12/178,979

(22) Filed: Jul. 24, 2008

(65) Prior Publication Data

US 2009/0030408 A1 Jan. 29, 2009

(30) Foreign Application Priority Data

Jul. 28, 2007 (EP) .................................. 07014856

(51) Int. Cl.
*A61B 18/20* (2006.01)
(52) U.S. Cl. .............................. 606/10; 607/88; 607/89; 606/9
(58) Field of Classification Search ............... 606/9–15; 607/88, 89
See application file for complete search history.

(56) References Cited

U.S. PATENT DOCUMENTS

| | | | |
|---|---|---|---|
| 4,852,551 A * | 8/1989 | Opie et al. ................... 600/121 |
| 5,474,549 A | 12/1995 | Ortiz et al. |
| 5,575,756 A * | 11/1996 | Karasawa et al. ........... 600/157 |
| 5,643,253 A * | 7/1997 | Baxter et al. .................. 606/17 |
| 5,725,521 A | 3/1998 | Mueller |
| 5,860,968 A | 1/1999 | Wojcik et al. |
| 2003/0036680 A1 | 2/2003 | Black |
| 2004/0249370 A1 * | 12/2004 | Berna et al. ................... 606/14 |
| 2006/0271028 A1 * | 11/2006 | Altshuler et al. ............... 606/9 |
| 2007/0129775 A1 | 6/2007 | Mordaunt et al. |
| 2008/0215039 A1 * | 9/2008 | Slatkine et al. ................ 606/9 |

FOREIGN PATENT DOCUMENTS

| | | |
|---|---|---|
| DE | 19510939 | 9/1996 |
| EP | 0933096 A2 | 8/1999 |
| EP | 1138269 | 10/2001 |
| EP | 1279374 | 1/2003 |
| WO | 03/041623 A1 | 5/2003 |

* cited by examiner

*Primary Examiner*—Henry M Johnson, III
*Assistant Examiner*—Jeffrey B Lipitz
(74) *Attorney, Agent, or Firm*—Gundrun E. Huckett

(57) ABSTRACT

A laser system has a laser source generating a laser beam, wherein the laser source is adapted for medical removal of body tissue by the laser beam within a predetermined treatment contour. A guide frame in the shape of the treatment contour is provided. A scanner is provided for completely scanning a base surface of the guide frame with the laser beam, wherein the scanner is arranged between the laser source and the guide frame in a path of the laser beam.

23 Claims, 4 Drawing Sheets

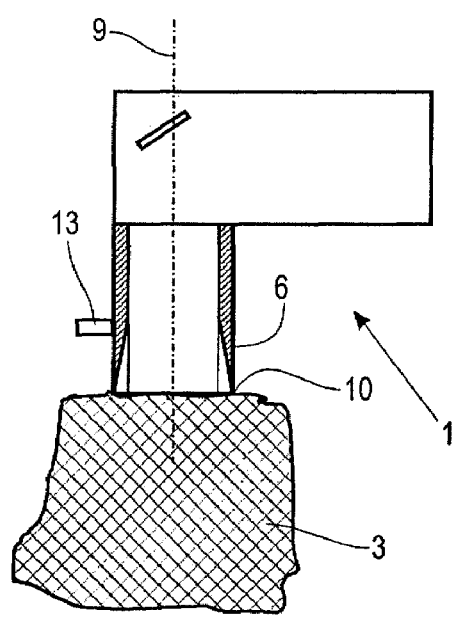
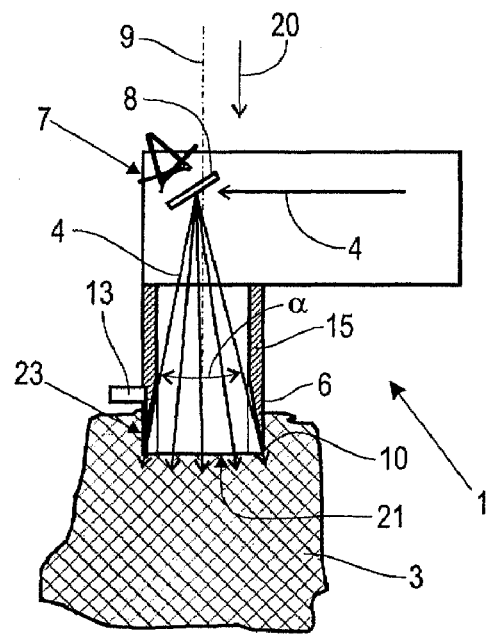
Fig. 7
Fig. 8
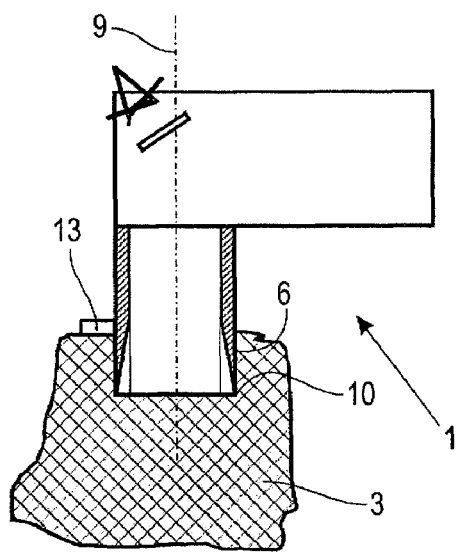
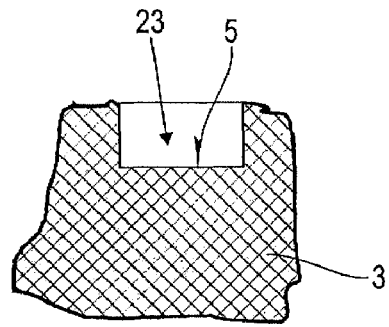
Fig. 9
Fig. 10

LASER SYSTEM FOR MEDICAL REMOVAL OF BODY TISSUE

BACKGROUND OF THE INVENTION

The invention relates to a laser system for medical removal of body tissue with a laser source for medical removal of body tissue by means of a laser beam within a predetermined treatment contour. The invention further relates to a method for operating such a laser system.

Classical surgical means to remove or shape soft or hard human tissue (including but not limited to the osseous (bone) tissue) are mechanical drills and saws. The advantage of these tools is that the surgeon has a very good tactile contact with the treated tissue providing feedback to the surgeon regarding the speed of the procedure and the depth of the drilled hole or the cut.

The mechanical means are disadvantageous because of the generated heat and thermal damage to the tissue as well as a smear layer that is left on the surface of the treated tissue. This leads to a delay in wound healing and compromised blood circulation. In order to minimize thermal damage to the tissue, the holes in the tissue are made by slowly drilling several holes of increasing diameter into the tissue, starting first with a small diameter drill. This makes the procedure very slow and also imprecise. Another disadvantage is the relatively great mechanical pressure that needs to be applied on the tissue in order to perform mechanical tissue removal. Disadvantageous are also the physical limitations with regard to achievable shape or size of the cuts and/or drilled holes. For example, it is not possible to achieve cuts in an exact zigzag pattern or other pattern that would be desirable e.g. for inserting implants in bone tissue in order to increase the bonding surface area.

In contrast to conventional mechanical methods, a manually performed non-contact laser surgery allows to ablate tissue in a shape that can be individually adapted to the clinical situation. Moreover, the laser allows arbitrary and sophisticated cut geometries with unprecedented preciseness. In addition, the cuts are clean and without the mechanically and thermally induced smear layer. However, the main disadvantage of laser surgery has been the difficulty in positioning the non-contact laser hand piece on the treated tissue and in obtaining a quick and reliable feedback with regard to the achieved depth of the laser cut or drilled hole. For this reason, laser-assisted surgery has not gained wide acceptance in the medical community.

SUMMARY OF THE INVENTION

The invention has the object to further develop a laser system of the aforementioned kind such that its handling is improved while high efficiency is provided.

This object is solved by a laser system comprises a guide frame in the shape of the treatment contour, wherein a scanner is provided for completely scanning a base surface of the guide frame by means of the laser beam, wherein the scanner is arranged between the laser source and the guide frame in the path of the laser beam.

The invention additionally has the object to provide an improved method for operating a laser system with increased exactness and efficiency.

This object is solved by a method comprising the following steps:

the guide frame is placed on a surface of the body tissue;
the treatment contour is scanned by the laser beam by means of the scanner, resulting in the formation of a recess in the body tissue by ablation of the body tissue in the shape of the treatment contour and the guide frame;
successively inserting the guide frame into the recess along with increasing ablation depth until the desired ablation depth has been reached.

A laser system and a method of operating the laser system are proposed, wherein the laser system has a guide frame in the shape of the treatment contour. Between the laser source and the guide frame, a scanner is arranged in the path of the laser beam for scanning the base surface of the guide frame with the laser beam. In operation, the laser system is placed with its guide frame onto the tissue to be removed. By action of the scanner the base surface of the guide frame is scanned completely by means of the laser beam. The guide frame delimits precisely the surface area that is scanned by the laser beam so that the tissue is removed across the surface area precisely relative to the contour. By means of the guide frame that is in particular guided by hand, the user has direct contact with the surface to be treated. The user can therefore develop a sense for the surface pressure and axial advancing speed. There is a tactile feedback of the treatment progress. The laser beam removes the tissue exactly within the contour that is defined by the guide frame so that the guide frame penetrates also into the tissue with increasing depth of tissue removal. The removed recess provides in this connection a lateral guiding action for the guide frame that can be sensed by the user so that lateral slipping is prevented. Even for great removal depths, the predetermined treatment contour is maintained within the tissue. Handling is significantly facilitated. While providing the greatest possible gentle treatment of the surrounding tissue, it is possible to generate great advancing speeds.

In a preferred embodiment, a mirror of the scanner is arranged near the central axis of the guide frame wherein a maximum deflection angle of the mirror is adjusted such that the laser beam impinges in a slanted outward direction onto an edge of the guide frame that is facing the body tissue. In this way, it is ensured that the laser beam not only removes tissue within the central area of the base surface of the guide frame but also along the edge of the guide frame. With an appropriate adjustment, the orientation of the laser beam at a slant outwardly has the result that the removed treatment contour is slightly larger than the base surface of the guide frame. In this way it is ensured that the guide frame can penetrate into the recess of the tissue that is being produced with slight oversize.

In a preferred embodiment, the guide frame has on its inner side a circumferentially extending slanted surface that widens in the radial and axial directions and ends at the pointed edge. In this way, it is ensured that the guide frame does not cover, not even in the edge area, sections of the treatment contour relative to the laser beam. The base surface of the guide frame and the treatment contour match one another with greatest possible precision.

In an advantageous further embodiment, a focus of the laser beam is positioned at least approximately on the base surface of the guide frame. At its focus, the laser beam has its maximum energy density and thus the greatest removal action. At the exit side of the focus, the energy density and thus also the removal action decrease. In this way, it is achieved that the location of actual tissue removal coincides approximately with the base surface of the guide frame, i.e., it is substantially not advanced relative to the penetration of the guide frame. Geometric deviations between the treatment contour and the base surface of the guide frame that are caused, for example, by angular errors due to the laser beam impinging at a slant across portions are minimized.

The guide frame has advantageously a depth mark in particular in the form of a depth stop. Based on, for example, a depth scale, the user can check the penetration depth during treatment and, in this way, can check the progress of the treatment. The depth stop can be adjusted at a desired position in order to achieve precisely the predetermined penetration depth without surpassing it or not reaching it.

In a preferred embodiment, the guide frame forms an end of a closed guide tube that guides the laser beam. In this way, the treatment area is protected from undesirable external influences. Alternatively, it can be expedient to arrange the guide frame at one end of an open support. In this way, the person performing the treatment can perform additional interventions on the treated tissue. For example, rinsing and/or cooling of the treated tissue area with water or other suitable liquids can be done during treatment through an open support. Moreover, a visual control of the treatment surface is possible through the open support and the guide frame.

In an advantageous embodiment, a protective window is arranged on an input side of the guide frame, and a cleaning channel is provided for delivering water and/or air. The delivery direction of said cleaning channel is oriented to an output side of said protective window. The cleaning channel can deliver either water or air, or a mixture of both to the protective window in order to clean the window from the debris, and/or to moisturize the debris in order to prevent that the debris is baked to the window.

In a preferred embodiment, an air channel is provided, the delivery direction of said air channel being oriented to the treatment area. The air channel can provide air to the ablated area in order to blow the collected water, blood or other bodily fluids away from the treatment site.

The delivery direction of said cleaning channel and the delivery direction of said air channel are advantageously crossing each other. When the air is turned off, the water from the cleaning channel is directed to the protective window for cleaning and/or moistening. When the air is on, the water gets pulled down by the air to the treatment site. With a small amount of design and manufacturing effort, numerous different tasks can be performed.

In an advantageous embodiment, an air channel is provided, the delivery direction of said air channel being oriented generally parallel across the output side of said protective window. The air channel can deliver air to the output side surface of the protective window for cleaning the window by blowing away the debris.

In a preferred embodiment the guide frame is embodied as a geometric prism. The prism can be an inclined prism which enables a slanted penetration of the guide frame into the body tissue. Preferably, the prism is a right prism so that advancement perpendicular to the base surface of the guide frame is possible. The prism configuration, i.e., a configuration in which the surface area of the transverse section taken along the longitudinal axis remains the same, enables, on the one hand, an unhindered penetration of the guide frame into the body tissue, and, on the other hand, results in the circumferential surface of the guide frame resting flat against the circumferential surface of the recess in the body tissue generated by the laser beam. With increasing removal depth the flat contact causes the precision of the guiding action to increase. Great treatment depth can be generated with minimal lateral displacement errors.

In an advantageous further embodiment, an at least approximately constant advancing force is provided that acts on the guide frame in the direction of its longitudinal axis. This advancing force can be, for example, the weight force of the laser system or a manually applied force exerted by the trained user. During treatment, no advancing speed but only an advancing force is thus exerted. In this way, it is taken into account that the tissue to be removed has in the direction of depth a changing density, hardness or other property that is noticeable as varying removal quantities per time unit. By providing the advancing force as the control parameter, a self-regulating advancing speed that depends on the respective removal progress will be automatically adjusted.

In a preferred embodiment of the method, after the desired ablation depth and insertion depth of the guide frame into the recess has been reached, an additional bottom cavity is ablated by the laser beam. The cavity provides space for bodily liquids and blood when an implant is inserted, or allows space for the specially shaped implant itself.

In an advantageous further embodiment, during the initial period of the ablation procedure, the treatment contour is scanned in such a way, that at least one spot located at the border of the treatment contour remains not ablated, and that the guide frame rests on the at least one spot. Preferably in total three spots remain not ablated. During the initial period of the ablation procedure, the recess is not deep enough to sufficiently provide guidance for the guide frame. The spots make sure that the guide frame remains perpendicular to the scanned plane throughout the initial scan. The risk that the recess will not be ablated evenly and that the guide frame will not fall into the recess perpendicularly to the scanned plane is impaired.

BRIEF DESCRIPTION OF THE DRAWINGS

Embodiments of the invention will be explained in more detail in the following with the aid of the drawing.

FIG. 7 shows in a schematic longitudinal section illustration the arrangement according to FIG. 1 as it is being placed onto body tissue exemplified by bone material.

FIG. 8 shows the arrangement according to FIG. 7 in operation during immersion into the body tissue.

FIG. 9 shows the arrangement according to FIGS. 7 and 8 as it reaches the predetermined treatment depth.

FIG. 10 shows the body tissue according to FIGS. 7 to 9 with contour-precisely removed material after removal of the laser system.

DESCRIPTION OF PREFERRED EMBODIMENTS

Figure 1:
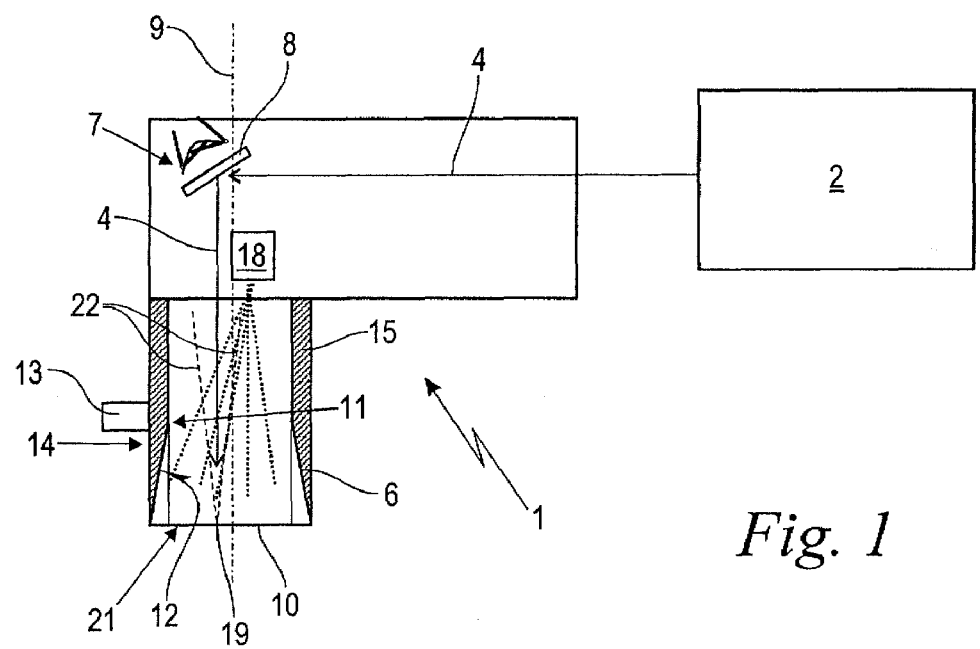
FIG. 1 shows in a schematic longitudinal section illustration a laser system according to the invention comprising a scanner and a guide frame at the end of a guide tube.

FIG. 1 shows in a schematic longitudinal section illustration an embodiment of a laser system 1 according to the invention for medical removal of body tissue 3 that is schematically indicated in FIGS. 4 through 7. The laser system 1 comprises of laser source 2, a scanner 7, as well as a guide frame 6. The laser source 2 generates a laser beam 4 with which in operation body tissue 3 (FIGS. 4 through 7) is removed. The scanner 7 is arranged in the path of the laser beam 4 between the laser source 2 and the guide frame 6. The laser beam 4 impinges on a mirror 8 of the scanner 7 and is deflected by it by approximately 90 degrees. The mirror 8 of the scanner 7 is controllable in such a way that the reflected laser beam 4 can be deflected in different directions. By an appropriate control of the scanner 7, a base surface 21 of the guide frame 6 is scanned by means of the exiting laser beam 4.

In the illustrated embodiment, the guide frame 6 forms the end 14 of a closed guide tube 15 that guides the laser beam 4 exiting from the scanner 7. The guide frame 6 and the guide tube 15 are configured as a geometrically right prism with a central axis 9. The scanner 7 is arranged close to the central axis 9 wherein the central axis 9 in the illustrated embodiment passes through the mirror 8 of the scanner 7.

The guide frame 6 has on the side facing the body tissue 3 to be treated (FIGS. 4 through 7) a closed circumferentially extending edge 10 that delimits the base surface 21 of the guide frame 6. In the illustrated embodiment the edge 10 is a pointed edge. For this purpose, the guide frame 6 has on its inner side 11 a circumferentially extending slanted surface 12 that, beginning at the scanner 7, widens in the radial and axial directions and ends at the pointed edge 10. The outer circumferential surface of the guide frame 6 and the guide tube 15 is of such a prism shape that its cross-section at any location of the central axis 9 is identical to the base surface 21.

By a suitable control of the scanner 7, the base surface 21 of the guide frame 6 is completely scanned or illuminated by the laser beam 4 exiting from the mirror 8. By means of a non-represented optical device, the laser beam is provided with a focus 19 that, relative to the central axis 9, is at least approximately positioned on the base surface 21 of the guide frame 6. The generation of the focus 19 is indicated schematically by the schematically shown boundary rays 22 of the laser beam 4. By actuation of the scanner 7, the focus 19 migrates on the base surface 21 without however leaving noticeably the base surface 21 in the depth direction, i.e., in the direction of the central axis 9.

On the exterior circumferential surface of the guide tube 15 and/or of the guide frame 6 a depth mark is arranged that will be explained infra in more detail. The depth mark can be embodied as a scale or the like and is embodied as a depth stop 13 in the illustrated embodiment. Moreover, the illustration of FIG. 1 also shows that in the laser system 1 a schematically illustrated spraying device 18 is provided with which cooling or rinsing water can be sprayed onto the surface to be treated.

Figure 2:
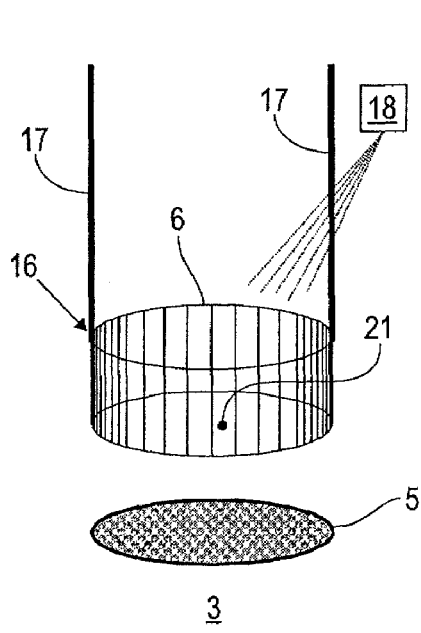
FIG. 2 is a perspective schematic illustration of a cylindrical guide frame at the end of an open support.

FIG. 2 shows in a perspective schematic illustration an embodiment of a cylindrically configured guide frame 6 that has at its end 16 an open support 17. The open configuration of the support 17 makes it possible to arrange the spraying device 18 externally so that cooling or rinsing liquid can be supplied from the exterior into the interior of the guide frame 6 and thus to the treatment location.

Figure 3:
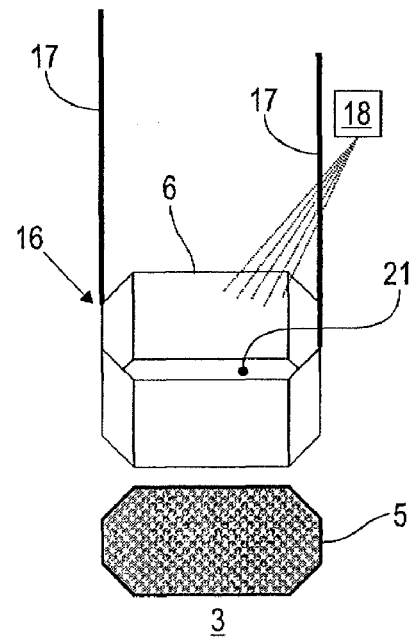
FIG. 3 shows a variant of the arrangement according to FIG. 2 with a guide frame in the form of a polygon.

As in the embodiment according to FIG. 1, the cylindrical guide frame 6 has a circular disk-shaped base surface 21 that, with regard to its shape, matches exactly a treatment contour 5 of the body tissue 3; this will be explained in more detail infra. In the embodiment according to FIG. 3, for illustrating the principle of the invention, a base surface 21 and a treatment contour 5 in the form of a polygon, here in an exemplary fashion in the form of an octagon, are illustrated. Depending on the treatment objective, almost any base surface 21 and, as a consequence, any identical treatment contour 5 can be preselected by means of the geometric configuration of the guide frame 6. In regard to other features and reference numerals, the embodiments according to FIGS. 2 and 3 are identical relative one another as well as relative to FIG. 1.

Figure 4:
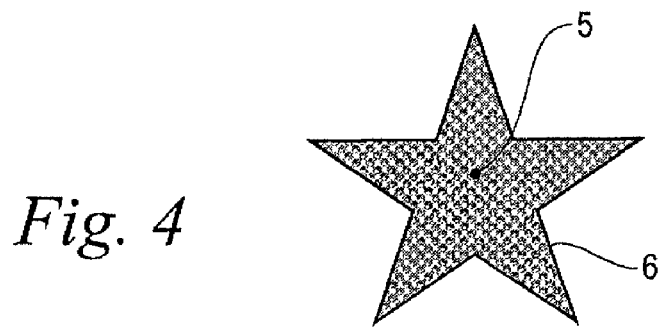
FIG. 4 is a schematic plane view of a star shaped guide frame.

A schematic plan view of a star shaped guide frame 6 to achieve a star shaped treatment contour 6 is shown as an example in FIG. 4. With this embodiment, star shaped or the like holes can be ablated specifically in hard body tissue like bone for the insertion of implants. The star shape supports the mechanical anchorage of the implant in the bone tissue.

Figure 5:
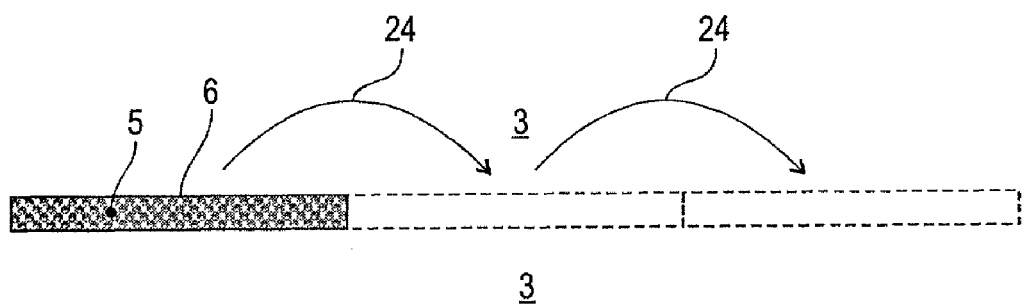
FIG. 5 is a schematic plane view of a rectangular guide frame for performing straight cuts.
Figure 6:
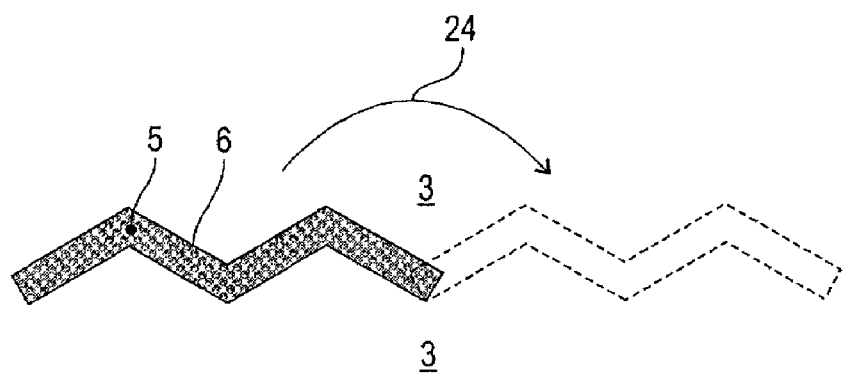
FIG. 6 is a schematic plane view of a zigzag shaped guide frame for performing zigzag shaped cuts.

FIG. 5 shows a schematic plane view of a rectangular guide frame 5 for performing straight cuts. With the narrow rectangular guide frame 5, narrow rectangular treatment contours 6 can be ablated. By moving and sequentially operating the rectangular guide frame 5 as indicated by arrows 24, straight cuts can be performed in the body tissue 3. Alternatively, the rectangular guide frame 5 may be turned back and forth by a predetermined angle around an axis perpendicular to the treatment contour 6, in order to perform zigzag cuts as shown in FIG. 6. Alternatively, a zigzag shaped guide frame 5 for performing zigzag shaped cuts may be used, as is schematically shown in FIG. 6.

FIGS. 7 through 11 show as phase images further details of the arrangement according to FIG. 1 and the method steps to be performed therewith. The treatment objective is to introduce a recess 23 (FIG. 7) or a cut (FIG. 5, 6) into living body tissue 3 in that by means of a laser beam 4 material is removed from the body tissue 3. Depending on the type of application, the user determines a treatment contour (FIG. 2 to 6, 10, 12). The recess 23 in this connection should have a base surface in the form of the treatment contour 5. The body tissue 3 can be bone material into which, for example, an implant is to be inserted. The recess 23 (FIG. 10) is to be generated for this purpose with a treatment contour 5 that should receive the implant with a fit as precise as possible. In order to achieve this, a guide frame 6 with the corresponding identical base surface 21 (FIGS. 2, 3) is inserted. The application of the inventive laser system 1 is however not limited to the treatment of bone material as body tissue 3. Other hard or soft body tissue 3 of the human body or animal body can be treated by means of the inventive laser system 1.

After selecting a suitable guide frame 6 with regard to its base surface 21 (FIGS. 2, 3), the laser system 1 is positioned such that the circumferentially extending edge 10 of the guide frame 6 rests on the surface of the body tissue 3 (FIG. 7). In this connection, the depth stop 13 has a spacing relative to the surface of the body tissue 3 in the direction of the central axis 9.

In accordance with the representation of FIG. 4, the laser source 2 (FIG. 1) is started so that a laser beam 4 is generated. With a controlled pivoting action of the mirror 8, the base surface 21 of the guide frame 6 is completely scanned or illuminated with the laser beam 4 reflected on the mirror 8. The maximum deflection angle α of the mirror 8 is selected such that during the course of the scanning process the laser beam 4 impinges, oriented at a slant outwardly relative to the central axis 9, on the edge 10 of the guide frame 6 which edge is facing the body tissue 3. This is enabled by the slanted surface 12 (FIG. 1) extending circumferentially in the area of the pointed edge 10. By means of scanning of the entire base surface 21 with the laser beam 4 as a result of actuation of the scanner 7, material of the body tissue is completely removed across the entire surface area including the area of the edge 10. This produces a recess 23 illustrated in FIG. 10. The base surface of the recess is identical to the treatment contour 5 that is predetermined by the base surface 21 of the guide frame 6. Because the base surface 21 of the guide frame 6 and the treatment contour 5 (FIG. 10) are substantially identical, the guide frame 6 will penetrate by the same amount and with the same speed into the body tissue 3 as material is removed in the area of the recess 23. According to the illustration of FIG. 8, it can be seen that the guide frame 6 in this connection is guided by its outer circumferential surface within the outer circumferential surface of the recess 23 in the direction of the central axis 9 and is secured with respect to lateral displacement. The control of the advancement of the laser system 1 is not realized by means of a predetermined advancing speed. Instead, an at least approximately constant advancing force 20 is provided that acts in the direction of the longitudinal axis 9 on the guide frame 6. This advancing force 20 can be, for example, the own weight of the laser system 1. Based on the power of the laser beam 4 and the resistance of the body tissue 3 in connection with a constant advancing force 20 a self-regulating advancing speed will result.

In accordance with the illustration of FIG. 8 the desired removal depth in the body tissue 3 has not been reached. The actual reached depth can be determined with the aid of a depth mark provided on the exterior side of the guide frame 6 or the guide tube 15. The depth stop 13 still has a spacing from the surface of the body tissue 3. As soon as the depth stop 13 rests against the surface of the body tissue 3, in accordance with the illustration of FIG. 9, i.e., the desired treatment depth has been reached, the laser beam 4 is turned off. Subsequently, the laser system 1 is removed wherein, in accordance with the illustration of FIG. 10, the recess 23 with the desired treatment contour 5 according to the base surface 21 of the guide frame 6 (FIGS. 2, 3, 8) is provided in the body tissue 3. The recess 23 is thus prepared for further treatment, for example, for insertion of an implant.

Figure 11:
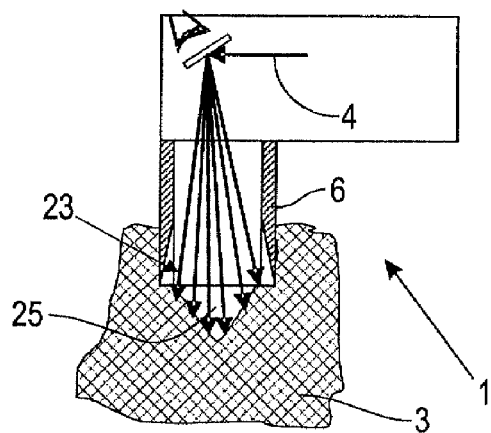
FIG. 11 shows the arrangement according to FIGS. 7 to 9 as it has reached the predetermined treatment depth, additionally ablating a bottom cavity.

FIG. 11 shows the arrangement according to FIGS. 7 to 9 as the guide frame 6 has reached the predetermined treatment depth, additionally ablating a bottom cavity 25. The laser beam 4 can be programmed to scan further within the boundaries of the guide frame 6 and recess 23 in a controlled manner in order to make the additional cavity 25 in a programmed shape. The role of this cavity 25 can be to provide space for bodily liquids and blood when an implant is inserted, or to allow space for the specially shaped implant itself.

Figure 12:
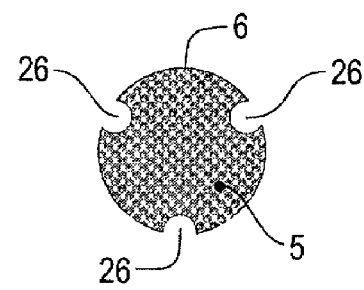
FIG. 12 is a schematic plane view of a circular shaped guide frame with three spots of the circular treatment contour remaining not ablated during the initial period of the ablation process.

A schematic plan view of a circular shaped guide frame 6 with three spots 26 of the circular treatment contour 5 is shown in FIG. 12. In laser drilling there is a risk that the recess 23 (FIG. 10, 11) will not be ablated evenly and that the guide frame 6 will not fall into the hole perpendicularly to the scanned plane. As shown in FIG. 12, the treatment contour 5 is scanned in such a way, that initially three spots 26 located at the borders of the scanned area remain not ablated. The guide frame is manually pressed against the three spots 26 to rest against them. These three spots 26 make sure that the guide frame 6 remains perpendicular to the scanned plane throughout the initial scan. As the whole treatment contour 5, apart from the spots 26, has been scanned for a while and a certain ablation depth has been achieved, the three spots 26 are ablated last, and the guide frame 6 can be pushed deeper into the body tissue 3 to the bottom of the recess 23. Then the scan procedure is repeated again without remaining spots 26, making use of the recess walls guiding the guide frame 6. In the preferred embodiment of FIG. 12 three spots 26 are shown. Different quantities of spots 26, at least one spot 26, may be desirable.

Figure 13:
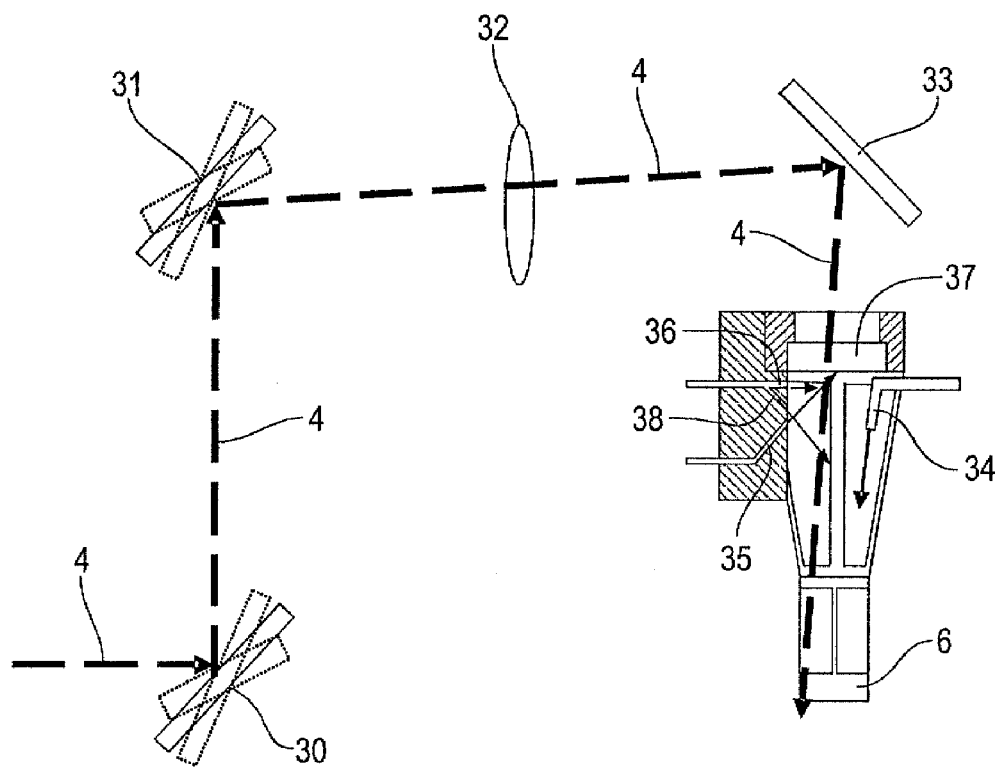
FIG. 13 shows in a schematic longitudinal section illustration an additional embodiment of the invention comprising multiple scanner mirrors and water-/air-channels in the vicinity of the guide frame.

FIG. 13 shows in a schematic longitudinal section illustration an alternative embodiment of the invention. In the embodiment depicted in FIG. 13, the laser beam 4 is directed by two scanner mirrors 30 and 31 that can rotate around axes that are perpendicular to each other, (or by a single mirror 31 that can rotate freely in all directions) through an optical focusing element 32 either by means of an additional bending mirror 33 or directly into the guide frame 6. A protective window 37 is arranged on an input side of the guide frame 6, in order to protect the interior of the hand piece with the laser system from debris and liquid, which sprays around during the ablation process of the body tissue 3 (FIG. 7 to 11).

The guide frame 6 or a hand piece with such a guide frame 6 is equipped with additional channels 34, 35, 36 for delivering air and water. A cleaning channel 35 is provided for delivering water and/or air. The delivery direction of said cleaning channel 35 is oriented to an output side of the protective window 37, as indicated by a respective arrow.

The cleaning channel 35 can deliver either water or air, or a mixture of both to the protective window 37 in order to clean the window from the debris, and/or to moisturize the debris in order to prevent that the debris is baked to the window by the heat of the laser beam 4.

In addition, an air channel 38 is provided, the delivery direction of said air channel 38 being oriented to the treatment area. It can provide air to the ablated area in order to blow the collected water, blood or other bodily fluids away from the treatment site. The delivery direction of the cleaning channel 35 and the delivery direction of the air channel 38 are crossing each other, as depicted by respective arrows. The air flow of the air channel 38 can be operated in pulses. When the air is turned off, the water from the cleaning channel 35 is directed to the output surface of the protective window 37. When the air is on, the water gets pulled down by the air to the treatment site.

A further air channel 36 is provided, its delivery direction being oriented generally parallel an across the output surface of the protective window 37. The air channel 36 can deliver air to the output side surface of the protective window for cleaning the window by blowing away debris and liquid. There can also be one or more additional water, air or water/air mixture channels 34, that are directed approximately perpendicular towards the treatment site.

The specification incorporates by reference the entire disclosure of European priority document 07 014 856.4 having a filing date of 28 Jul. 2007.

While specific embodiments of the invention have been shown and described in detail to illustrate the inventive principles, it will be understood that the invention may be embodied otherwise without departing from such principles.

What is claimed is:
1. A laser system comprising:
   a laser source generating a laser beam, wherein the laser source is adapted for medical removal of body tissue by the laser beam within a predetermined treatment contour;
   a guide frame providing a central axis, an outer circumferential surface and, on a side of the guide frame that is facing the body tissue, a circumferentially extending edge, wherein the circumferentially extending edge is pointed and defines a base surface of the guide frame matching exactly the shape of the treatment contour;

wherein the outer circumferential surface of the guide frame has a cross-section that is identical to the base surface and the treatment contour;

wherein the laser beam is provided with a focus that relative to the central axis is at least approximately positioned on the base surface of the guide frame;

a scanner being adapted for completely scanning said base surface of the guide frame with the laser beam for removing the body tissue, wherein the scanner has a mirror and the mirror is arranged near a central axis of the guide frame, wherein a maximum deflection angle is adjusted such that the laser beam, oriented at a slant outwardly away from the central axis impinges on the pointed edge, thereby causing a recess in the body tissue exactly within the contour that is defined by the base surface of the guide frame in such a way that the guide frame can be successively inserted into said recess with increasing depth of body tissue removal, wherein the focus migrates on said base surface without leaving noticeably said base surface in the direction of the central axis;

wherein the guide frame is adapted to be guided by said outer circumferential surface within an outer circumferential surface of the recess in the direction of the central axis of the guide frame and thereby being secured with respect to lateral displacement;

wherein the scanner is arranged between the laser source and the guide frame in a path of the laser beam.

2. The laser system according to claim 1, wherein the guide frame has an inner side that has a circumferentially extending slanted surface that, in an axial direction from the scanner to the edge, widens in a radial direction, wherein the slanted surface ends in the pointed edge.

3. The laser system according to claim 1, wherein a focus of the laser beam at least approximately is positioned on the base surface of the guide frame.

4. The laser system according to claim 1, wherein the guide frame has a depth mark.

5. The laser system according to claim 4, wherein the depth mark is a depth stop.

6. The laser system according to claim 1, further comprising a circumferentially closed guide tube connected to the scanner for guiding the laser beam, wherein the guide frame forms an end of the circumferentially dosed guide tube.

7. The laser system according to claim 1, further comprising an open support connected to the scanner, wherein the guide frame is arranged at an end of the open support opposite the scanner.

8. The laser system according to claim 1, further comprising a spraying device having a spraying direction oriented into the guide frame.

9. The laser system according to claim 8, wherein the spraying device sprays water for cooling and rinsing.

10. The laser system according to claim 1, further comprising a protective window arranged on an input side of the guide frame and moreover comprising a cleaning channel for delivering water or air or both water and air, wherein a delivery direction of the cleaning channel is oriented toward an output side of the protective window.

11. The laser system according to claim 10, further comprising an air channel having a delivery direction oriented toward the treatment area.

12. The laser system according to claim 11, wherein the delivery direction of the cleaning channel and the delivery direction of the air channel cross each other.

13. The laser system according to claim 10, further comprising an air channel having a delivery direction oriented generally parallel across the output side of the protective window.

14. The laser system according to claim 1, wherein the guide frame is configured as a geometric prism.

15. The laser system according to claim 14, wherein the geometric prism is a right prism.

16. The laser system according to claim 1, wherein several of said guide frame are provided that differ from one another by having different base surfaces, respectively, wherein, depending on a treatment objective with a desired treatment contour, one of said guide frames is selected whose base surface matches the desired treatment contour.

17. The laser system according to claim 1, wherein the cross-section of the outer circumferential surface of the guide frame is at any location of the central axis identical to the base surface and the treatment contour.

18. A method for removing body tissue with a laser system, the laser system comprising:
a laser source generating a laser beam, wherein the laser source is adapted for medical removal of body tissue by the laser beam within a predetermined treatment contour;
a guide frame comprising a central axis, an outer circumferential surface and, on a side of the guide frame facing the body tissue, a circumferentially extending edge, wherein the circumferentially extending edge defines a base surface of the guide frame matching exactly the shape of the treatment contour; wherein the outer circumferential surface of the guide frame has a cross-section that is identical to the base surface and the treatment contour; wherein the laser beam is provided with a focus that relative to the central axis is at least approximately positioned on the base surface of the guide frame; and
a scanner being adapted for completely scanning said base surface of the guide frame with the laser beam, wherein the scanner is arranged between the laser source and the guide frame in a path of the laser beam, the method comprising the steps of:

placing the guide frame on a surface of the body tissue;

scanning with the scanner the treatment contour by the laser beam and ablating body tissue by the laser beam, thereby causing a recess with an outer circumferential surface in the body tissue, wherein the recess, the treatment contour and the base surface of the guide frame have the same outer circumferential contour;

successively inserting the guide frame into the recess with increasing depth of body tissue removal, wherein the focus migrates on the base surface without leaving noticeably the base surface in the direction of the central axis;

guiding the guide frame by said outer circumferential surface within said outer circumferential surface of the recess in the direction of the central axis of the guide frame and thereby being secured with respect to lateral displacement.

19. The laser-system method according to claim 14, providing an at least approximately constant advancing force that acts on the guide frame in the direction of a longitudinal axis of the guide frame.

20. The method according to claim 18, further comprising the step of, after the desired insertion depth of the guide frame into the recess has been reached, ablating an additional bottom cavity in the body tissue by the laser beam.

21. The method according to claim 18, wherein, during an initial period of ablating body tissue, the treatment contour is scanned in such a way, that at least one spot located within the guide frame close to a border of the treatment contour initially remains unablated, wherein the guide frame rests on the at least one spot, and that the at least one spot is ablated last.

22. The method according to claim 20, wherein the at least one spot comprises spots that remain unablated.

23. The method according to claim 18, comprising:
providing several of said guide frame that differ from one another by having different base surfaces, respectively, and, depending on a treatment objective with a desired treatment contour, selecting one of said guide frames whose base surface matches the desired treatment contour.

* * * * *